United States Patent
Cardoso de Lima et al.

(10) Patent No.: US 11,523,981 B2
(45) Date of Patent: Dec. 13, 2022

(54) COSMETIC COMPOSITION AND ITS USE, DERMOCOSMETIC FORMULATION

(71) Applicant: LUXBIOTECH FARMACÊUTICA LTDA, Jaguariuna (BR)

(72) Inventors: Erine Cardoso de Lima, Hortolândia (BR); Luiz Felipe de Oliveira Stehling, Hortolândia (BR); Silvana Masiero, Hortolândia (BR); Talitha Farina Bezerra, Hortolândia (BR)

(73) Assignee: LUXBIOTECH FARMACÊUTICA LTDA, Jaguariuna (BR)

( * ) Notice: Subject to any disclaimer, the term of this patent is extended or adjusted under 35 U.S.C. 154(b) by 195 days.

(21) Appl. No.: 16/723,230

(22) Filed: Dec. 20, 2019

(65) Prior Publication Data

US 2020/0197292 A1   Jun. 25, 2020

(30) Foreign Application Priority Data

Dec. 21, 2018 (BR) .................. 10 2018 076986 3

(51) Int. Cl.
*A61K 8/97* (2017.01)
*A61K 8/19* (2006.01)
*A61K 8/34* (2006.01)
*A61K 8/362* (2006.01)
*A61K 8/368* (2006.01)
(Continued)

(52) U.S. Cl.
CPC ............... *A61K 8/97* (2013.01); *A61K 8/19* (2013.01); *A61K 8/345* (2013.01); *A61K 8/362* (2013.01); *A61K 8/368* (2013.01); *A61K 8/37* (2013.01); *A61K 8/44* (2013.01); *A61K 8/55* (2013.01);
(Continued)

(58) Field of Classification Search
None
See application file for complete search history.

(56) References Cited

U.S. PATENT DOCUMENTS

| 5,980,904 | A | * | 11/1999 | Leverett | A61K 8/9789 |
|---|---|---|---|---|---|
| | | | | | 424/725 |
| 2013/0302265 | A1 | * | 11/2013 | Rana | A61K 8/9789 |
| | | | | | 424/62 |
| 2016/0067163 | A1 | * | 3/2016 | Meyer | A61Q 19/02 |
| | | | | | 424/59 |

OTHER PUBLICATIONS

Kobayashi, T. et al. "Tyrosinase related protein 1 (TRP1) functions as a DHICA oxidase in melanin biosynthesis", The EMBO Journal vol. 13 No. 24 pp. 5818-5825, 1994.

(Continued)

*Primary Examiner* — Bong-Sook Baek
*Assistant Examiner* — Barbara S Frazier
(74) *Attorney, Agent, or Firm* — Meunier Carlin & Curfman LLC

(57) ABSTRACT

The present invention refers to dermocosmetic formulations for use against skin blemishes, especially melasma. The present invention minimizes or avoids the formation of melasma by acting in several stages of melanogenesis.

A preferred embodiment of the invention refers to dermocosmetic formulations that act in several stages of melanogenesis, preferably, in the gene expression of tyrosinase-related proteins (TYRP-1 and TYRP-2) and Endothelin-1 (ET-1).

Another embodiment of the invention refers to the cosmetic composition containing a combination of active ingredients that act on the gene expression of tyrosinase-related proteins (TYRP-1 and TYRP-2) and Endothelin-1 (ET-1).

In another preferred embodiment of the invention, the use of said cosmetic composition to combat melasma is described.

25 Claims, 3 Drawing Sheets

(51) Int. Cl.
    *A61K 8/37*     (2006.01)
    *A61K 8/44*     (2006.01)
    *A61K 8/55*     (2006.01)
    *A61K 8/73*     (2006.01)
    *A61K 8/92*     (2006.01)
    *A61Q 19/02*     (2006.01)

(52) U.S. Cl.
    CPC ................ *A61K 8/73* (2013.01); *A61K 8/922* (2013.01); *A61Q 19/02* (2013.01); *A61K 2800/59* (2013.01)

(56) References Cited

OTHER PUBLICATIONS

Tsukamoto, K. et al. "A second tyrosinase-related protein, TRP-2, is a melanogenic enzyme termed DOPAchrome tautomerase". The EMBO Journal vol. 11 No. 2 pp. 519-526, 1992.

\* cited by examiner

COSMETIC COMPOSITION AND ITS USE, DERMOCOSMETIC FORMULATION

FIELD OF THE INVENTION

The present invention is directed to the development of a dermocosmetic formulation for use against skin blemishes, especially melasma. The present invention minimizes or avoids the formation of melasma through performance in various stages of melanogenesis, a process responsible for melanin synthesis, especially the dermocosmetic formulation of the present invention performs its function influencing transcription and/or activation of enzymes that favor the stages of melanogenesis.

BACKGROUND OF THE INVENTION

The skin is, in essence, a protective organ and the function that stands out is the protection against the physical damage caused by the sun. The physiological role of melanin consists fundamentally of providing skin color and chromophore absorption, generating natural photo-protection. As sunscreen, melanin differs or reflects UV radiation. After irradiation, the melanosome regroup around the nucleus and thus protect the genetic material of the cell.

Many are the pathological changes in skin color, which are called dyschromias. Melanins are heterogeneous biopolymers produced by specialized cells called melanocytes, which are found in the basal layer of the epidermis, follicular bulb and eyes. They are synthesized by melanogenesis and responsible for skin, hair and eye pigmentation.

The path of melanin production is the melanogenesis process, and can be modulated by regulating the expression and activity of enzymes. This regulation is determined by different biochemical agents, which are considered fundamental elements for the phenomenon of pigmentation.

Although melanin plays an important role for protection against UV radiation injury, its disordered production can lead to the formation of lentigo or senile purpura. In response to skin exposure to UV radiation, melanogenesis is increased by the activation of tyrosinase, a key enzyme in this process.

Tyrosinase is a metalloprotein located in the membrane of melanosome and catalyzes the first steps of melanin production: hydroxylation of L-tyrosine and L-dihydroxyphenylalanine (L-DOPA) and subsequent oxidation of o-diphenols by the corresponding quinone, L-dopaquinone.

Tyrosinase is initially synthesized on the surface of the rough endoplasmic reticulum, where it is then transferred to the Golgi complex, associated with lysosome and thus activated by the addition of a sugar chain before being secreted into a vesicle.

A pre-melanosome released from the Golgi complex joins with the vesicle to form the functional unit called melanosome. In the melanosome, tyrosinase converts tyrosine into (black) eumelanin or (yellowish or reddish) pheomelanin.

In addition, skin hyperpigmentation occurs due to several factors, including aging, pregnancy, endocrine disorders, treatment with sex hormones and sun exposure to different degrees. Many studies prove that sunlight radiation is the main cause for most dyschromias, followed by hormones and/or external factors. Thus, products capable of reducing melanin production present the potential to act as depigmenting agents.

Among the main ways of promoting skin whitening, the inhibition of enzymes that play an important role in melanin biosynthesis, inhibition of melanosome transport to keratinocytes and the reduction of the production of reactive oxygen species (ROS). Due to the central role of tyrosinase in the pigmentation process, most available depigmenting active ingredients perform their function by influencing transcription or activation of this enzyme, as well as other enzymes of melanogenesis TYRP-1 and TYRP-2. Here reference is made to articles by Kobayashi et al (1994)— Ref. 1, and from Tsukamoto et al (1992)—Ref. 2.

Endothelin-1 (ET-1), besides favoring the initial stages of melanosome formation, stimulates the growth of melanocytes, increases transcription and activity of tyrosinase and, consequently, melanin synthesis.

From this stage of the melanogenesis cascade, the presence or absence of cysteine determines the course of the reaction for the synthesis of eumelanin and pheomelanin. In the absence of cysteine, dopaquione is converted into cyclodopa and this, into dopachrome.

There are two ways to modify dopachrome: one that forms DHI (dopa, 5.6 dihydro indol) and another that forms DHICA (5.6 dihydroxyindole-2-carboxylic acid) in smaller quantity. The latter is generated by dopachrome tautomerization, a reaction catalyzed by TYRP-2. In this context, the TYRP-1 enzyme seems to be involved in the process of catalyzing eumelanin oxidation in DHICA.

In order to solve the problem of combating skin blemishes, especially melasma, various techniques and forms of non-therapeutic treatment are suggested in the literature and by another important segment, the cosmetic industry, which promotes treatments that use active ingredients incorporated into creams, cosmetic compositions, gels, elixirs, among others.

For example, the document PI0804089-3 reveals a topical composition for skin whitening. However, in that document, there are no teachings or data on the effect of composition on enzymes involved in melanogenesis.

Thus, the development of a dermocosmetic formulation that has whitening and depigmenting function through the action for this dermocosmetic formulation in enzymes that act on melanin production in the skin.

SUMMARY OF THE INVENTION

The present invention refers to dermocosmetic formulations for use against skin blemishes, especially melasma. The present invention minimizes or avoids the formation of melasma by acting in several stages of melanogenesis.

A preferred embodiment of invention refers to dermocosmetic formulations that act in several stages of melanogenesis, preferably, in the gene expression of tyrosinase-related proteins (TYRP-1 and TYRP-2) and Endothelin-1 (ET-1).

Another embodiment of the invention refers to the cosmetic composition containing a combination of active ingredients that act on the gene expression of tyrosinase-related proteins (TYRP-1 and TYRP-2) and Endothelin-1 (ET-1).

In another preferred embodiment of the invention, the use of the mentioned cosmetic composition to combat melasma is described.

Surprisingly, the inventors of the present invention identified an excellent performance of the formulations herein described in relation to the less traditional mechanisms in the formation of blemishes. In particular, these formulations present excellent activity in the expression of important enzymes in melanogenesis, in addition to the already known activity on tyrosinase.

These characteristics of the invention will be described in more details in the detailed description of the invention.

DETAILED DESCRIPTION OF THE INVENTION

In this description, a dermocosmetic formulation, a cosmetic composition and its use is presented to combat skin blemishes, especially melasma. This cosmetic composition comprises the combination of several whitening agents in addition to other components.

Surprisingly, the inventors of the present invention noted that this cosmetic composition acts in lesser known mechanisms of melanin production, more specifically, this cosmetic composition has activity in the gene expression of tyrosinase-related proteins (TYRP-1 and TYRP-2) and Endothelin-1 (ET-1).

The dermocosmetic formulation of the composition is prepared by combining several whitening agents.

Examples of whitening agents may be: α-arbutin, glucosyl hesperidin, gallic acid glucoside, *Hypoxis rooperi* rhizome extract, *Caesalpinia spinosa* Extract Gum, *Humulus lupulus* (hops) Strobile and decapeptide-4.

Preferably, the formulation of cosmetic composition is prepared by combining α-arbutin with glucosyl hesperidin, gallic acid glucoside, *Hypoxis rooperi* rhizome extract, *Caesalpinia spinosa* Extract Gum, *Humulus lupulus* (hops) Strobile and decapeptide-4.

In addition to whitening agents, other active ingredients may be additionally used. Polysaccharide ingredients such as Biosaccharide Gum-1 and Biosaccharide Gum-2 and amino acids such as (amino acids (arginine, aspartic acid, alanine, serine, valine, proline, isoleucine, threonine). These active ingredients improve the skin sensory by promoting hydration.

Melanogenesis

Melanogenesis occurs inside melanosome, where two types of melanin are synthesized: eumelanin, a dark brown to black insoluble polymer, and pheomelanin, a reddish or yellowish polymer that contains sulfur in its composition. Total skin melanin results from a mixture of eumelanin and pheomelanin monomers and the proportion between the two determines the final phenotypic expression of skin color. With exposure to ultraviolet radiation (UV), for example, melanogenesis is increased by activation of key enzymes such as tyrosinase.

Figure 1:
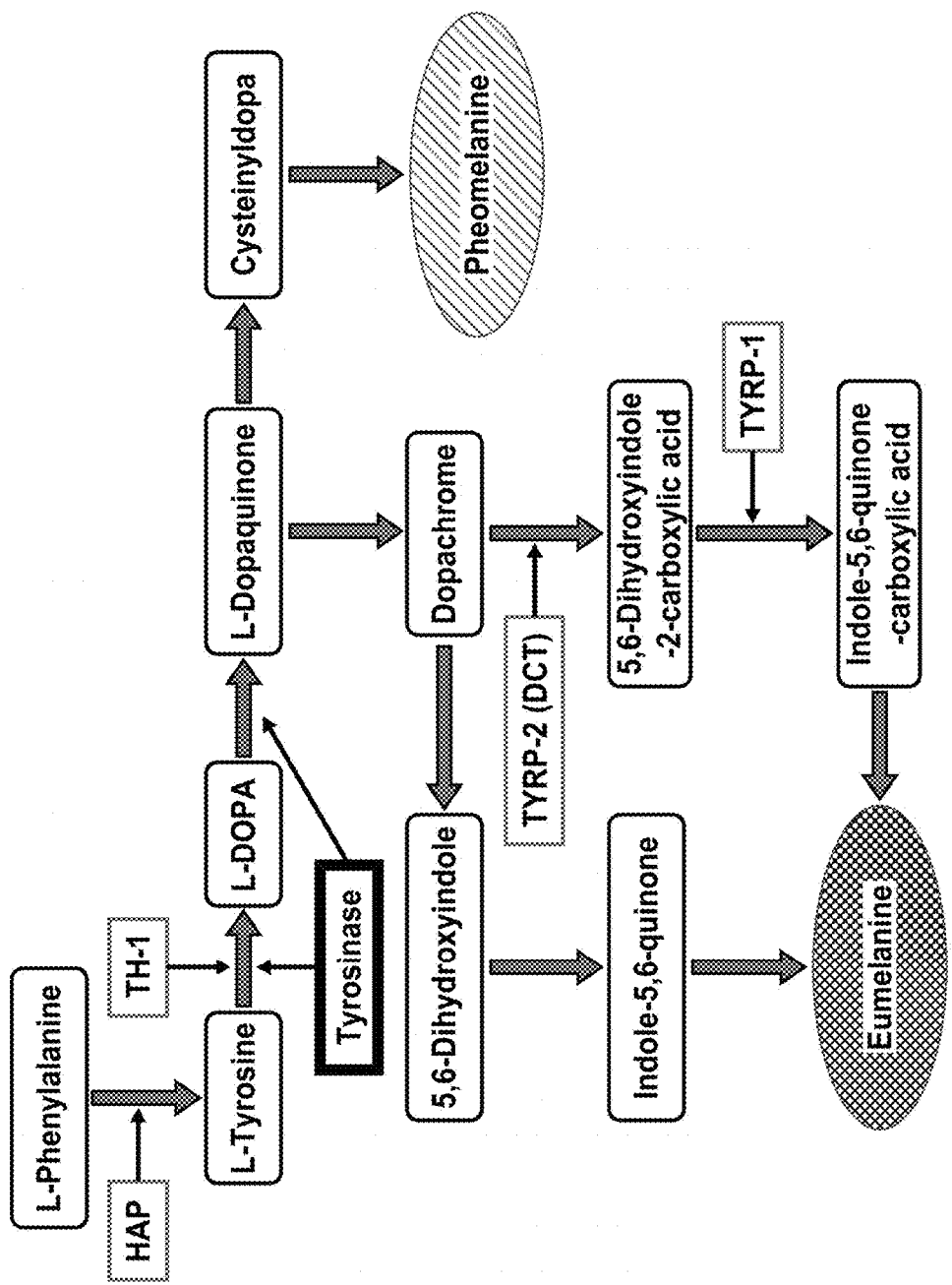
FIG. 1 presents a scheme of eumelanin and pheomelanin production with the performance of tyrosinase enzymes, and tyrosinase-related proteins (TYRP-1 and TYRP-2).

Tyrosinase is a multifunctional enzyme that contains copper and is the key enzyme in the first stage of the melanogenesis cascade. In addition to it, the enzymes related to tyrosinase (TYRP-1 and TYRP-2) also acts on melanogenesis, and are responsible for conducting specific reactions in the branches illustrated in the following figure. Thus, to induce depigmentation, the activity of such key enzymes of the melanogenesis process should be inhibited, according to FIG. 1.

Additionally, endothelin-1 (ET-1) is also important in this process. ET-1 is a protein that acts on melanocytes through a receptor-mediated signal transduction pathway, stimulating the proliferation of melanocytes, migration, dendrite formation and melanogenesis through transcriptional control of tyrosinase expression. Both inhibition of ET-1 expression and antagonistic action in the ET-1 receptor result in the impediment of melanogenesis before it begins. Therefore, the reduction of ET-1 activity results in inhibition of melanocytes dendricity and consequently inhibits melanin synthesis.

Thus, inhibition of the melanogenesis mechanism can take place in two ways:
   by inhibiting the activity of tyrosinase, TYRP-1, TYRP-2 or ET-1 enzymes at post-translational level;
   or by the influence on the mRNA transcription of these proteins.

The active principles of the dermocosmetic formulation, that is, the whitening agents, are selected from the group consisting of: α-arbutin, glucosyl hesperidin, gallic acid glucoside, *Hypoxis rooperi* rhizome extract, *Caesalpinia spinosa* Extract Gum, *Humulus lupulus* (hops) Strobile and decapeptide-4, as mentioned above.

The α-arbutin is a glycosylated hydroquinone derivative found in cranberries, blueberries, wheat and peas, and is known to only inhibit tyrosinase activity, by competitive and reversible bonding, without influencing the transcription of its mRNA. In addition, the cosmetic composition of the present invention also presents photo-protective agents in order to ensure protection for components in relation to ultra-violet radiation, chelation agents, in addition to cosmetically acceptable excipients.

The dermocosmetic formulation of the present invention containing α-arbutin and other whitening agents such as glucosyl hesperidin, gallic acid glucoside, *Hypoxis rooperi* rhizome extract, *Caesalpinia spinosa* Extract Gum, *Humulus lupulus* (hops) Strobile and decapeptide-4 as active ingredients, demonstrated strong inhibitory action in the activities of TYRP-1, TYRP-2 and TYRP-1, which implies in an amazing and unexpected result.

According to the present invention, the terms "active ingredient", "bulk active" and "active" are used interchangeably and refer to compounds in a cosmetic composition that promote a desired cosmetic effect.

According to the present invention, the term "cosmetically acceptable", refers to compounds that are commonly used in cosmetic technique together with active ingredients. In particular, "cosmetically acceptable" refers to compounds that check, without limitations, shape, scent, stability and coloring of the final cosmetic composition, safely and tolerable for a user of the final product. In some embodiments, a "cosmetically acceptable" component can make easier the absorption of one or more active ingredients under application.

Cosmetically acceptable excipients comprise, without limitations, surfactants, preservatives, conditioning agents, humectants, emollients, film-forming agents, hydrants, pH adjustment agents, chelation agents and vehicles.

Examples of pH adjustment agents include, without limitations, sodium hydroxide and citric acid.

Examples of conditioning agents include, without limitations, hydrogenated lecithin, biosaccharide gum-1, sodium PCA, arginine, aspartic acid, glycine, alanine, valine, proline, threonine, histidine, phenylalanine, biosaccharide gum-2, caprylic/capric triglyceride.

Examples of preservatives include, without limitations, phenoxyethanol, potassium sorbate, methylisothiazolinone, sodium benzoate, and their mixtures.

Examples of emollients include, without limitations, glycine.

Examples of moisturizers include, PCA.

Examples of film-forming agents include, without limitations, *Caesalpinia spinosa* Extract Gum.

Examples of humectants include, without limitations, glycerin, sodium lactate, propylene glycol.

Examples of surfactants include, without limitations, hydrogenated castor oil, sodium oleate.

Examples of sequestering agents include, without limitations, EDTA, disodium EDTA, tetrasodium EDTA and their mixtures.

Examples of vehicles include, without limitations, water, esters in general, mineral oil and vegetable oils and their mixtures, while in an emulsified system.

Cosmetic composition can be presented in several forms, including, without limitations, solution, suspension, cream, gel, lotion and serum. A person skilled in the art will recognize that the cosmetic form will be defined by the choice of cosmetically acceptable excipients and that the absorption/action of the different active ingredients may vary according to the selected cosmetic form.

The following are the concentration ranges for each component of the dermocosmetic formulation of the present invention.

Whitening agents are present in the formulation of the present invention in a concentration range between 1.0 and 5.0% (w/w).

On the other hand, pH adjustment agents are present in a concentration range between 0.05 and 2.0% (w/w).

Conditioning agents are present in a concentration range between 0.0001 to 10.0% (w/w).

Preservatives are present in a concentration range between 0.0083 and 5.0% (w/w).

Emollients are present in a concentration range between 0.003 and 5.0% (w/w).

While moisturizers are present in a concentration range between 0.02 to 10.0% (w/w).

On the other hand, film-forming agents are present in concentrations ranging from 0.03 to 5.0% (w/w).

The humectants are present in concentrations that also vary between 0.02 and 6.0% (w/w).

Surfactants are present in concentrations ranging from 0.0003 to 9.0%.

The sequestering (or chelation) agents are present in concentrations ranging from 0.05 to 0.3% (w/w).

Finally, the concentrations of vehicles range from 59.22 to 95% (w/w).

EXAMPLES

It should be understood that the examples and achievements described here in detail illustrate the present invention without, however, limiting its scope, and that various modifications or changes, in the light of them, will be suggestive to a person skilled in the art. Such equivalent achievements shall be included within the scope and range of the accompanying claims.

The experimental conditions adopted, through the use of human cells under optimal conditions of cultivation, are consistent with the current methodologies applied, accepted and validated by the international scientific community. Human cell cultures were commercially acquired from qualified and certified international companies.

Example 1: Effects on Gene Expression of Endothelin-1 (ET-I) on "Dark Pigmented" Human Melanocytes Culture Example 1.1: Melanocytes Culture "Dark pigmented" human melanocytes (HEM-DP) were sown in 75 cm$^2$ bottles, cultivated and expanded in humid greenhouse at 37° C. in the presence of 5% $CO_2$, using specific culture medium. Upon reaching confluence, the cells were sown in plates of 06 wells for further incubation with the composition and evaluation of the proposed parameter.

Example 1.2: Incubation with the Cosmetic Composition of the Invention

Cell cultures were incubated with 3 non-cytotoxic concentrations of the cosmetic composition of the invention (0.78; 0.39; 0.195% (w/v)), previously determined through the MTT technique. The cells were kept in contact with the composition for 24 hours for subsequent cell lysate collection, extraction and relative quantification of mRNA. The control group was evaluated in parallel.

Example 1.3: Gene Expression of Endothelin-1 by Real-Time PCR

After 24 hours of incubation with predetermined concentrations of the cosmetic composition of the invention, the total RNA was extracted using the PureLink™ RNA Mini Kit (Life Technologies) and quantified through spectrophotometry using NanoDrop Lite (Thermo Scientific). The RT-PCR assay was performed on the StepOnePlus (Applied Biosystems) equipment. To analyze the gene expression of Endothelin-1, a commercially available assay system (gene expression of TaqMan® assays was used; Endothelin-1: HS00174961_m1, Applied Biosystems), primer and probe based with proper basis. The test was performed using the 1-Step TaqMan® RNA-to-CT™ (Applied Biosystems) kit.

The test conditions were 48° C. for 30 minutes for reverse transcription, 95° C. for 10 minutes for activation of Ampli-Taq Gold® polymerase DNA, followed by 55 cycles of 94° C. for 15 seconds and 60° C. for 1 minute for denaturation and reheating, respectively. The relative amount of mRNA was calculated as described by Pfaffl (2001) and Livak & Schmittgen (2001).

Example 1.4: Statistical Analysis

For statistical analysis, variance analysis (ANOVA) was used. Dunnett's test was used when variance analysis detected significant differences between groups. In all the groups studied, those whose P values were less than 0.05 were considered statistically significant.

Example 1.5: Results

Figure 2:
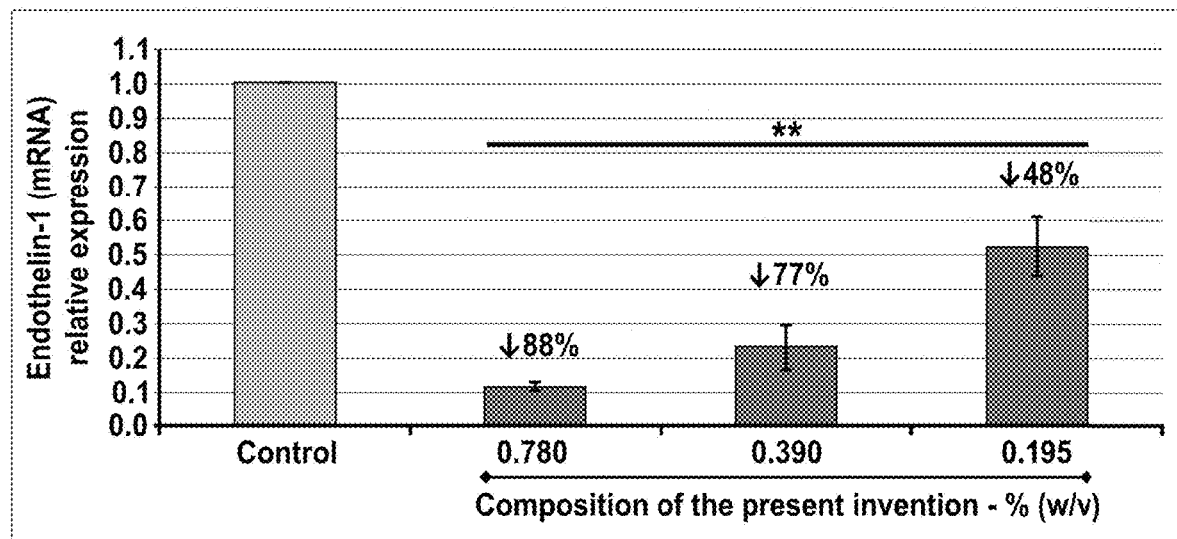
FIG. 2 shows a graph with the results of the effects of the composition of the present invention on the gene expression of Endothelin-1 in "dark pigmented" human melanocytes culture after 24 hours of incubation.

The results obtained, shown in Table 1 below, and FIG. 2, expose the relative gene expression (mRNA) of Endothelin- 1. It is possible to observe that the cosmetic composition of the invention, in the concentrations evaluated of 0.78, 0.39 and 0.195% (w/v), was able to significantly reduce the relative expression of Endothelin-1 in 88, 77 and 48%, respectively, in relation to the Control group.

TABLE 1

| Concentration (% (w/v)) | V1 | V2 | V3 | V4 | Average | DP |
|---|---|---|---|---|---|---|
| Control | 1.000 | 1.000 | 1.000 | 1.000 | 1.000 | 0.000 |
| 0.78 | 0.102 | 0.131 | 0.125 | 0.114 | 0.118 | 0.013 |
| 0.39 | 0.258 | 0.244 | 0.134 | 0.287 | 0.231 | 0.067 |
| 0.195 | 0.503 | 0.437 | 0.637 | 0.519 | 0.524 | 0.083 |

Example 2: Effects on the Gene Expression of TYRP-1 on Human Melanocytes Culture Example 2.1: Melanocytes Culture Human melanocytes were sown in 75 cm² bottles, cultivated and expanded in humid greenhouse at 37° C. in the presence of 5% $CO_2$, using a specific culture medium. When they reached confluence, the cells were sown in plates of 06 wells for further incubation with the test product and evaluation of the proposed parameter.

Example 2.2: Incubation with the Cosmetic Composition of the Invention

Cell cultures were incubated with 3 non-cytotoxic concentrations of the cosmetic composition of the invention (0.78; 0.39; 0.195% (w/v)), previously determined through the MTT technique. The cells were kept in contact with the composition for 24 hours with stimulation of melanin production, through incubation with ALFA-MSH (alpha melanocytes stimulating hormone) for subsequent cell lysate collection, extraction and relative mRNA quantification. In parallel, only one control group with ALFA-MSH was evaluated.

Example 2.3: Gene Expression of TYRP-1 by Real-Time PCR

After 24 hours of incubation with predetermined concentrations of the cosmetic composition of the invention, the total RNA was extracted using the PureLink™ RNA Mini Kit (Life Technologies) and quantified through spectrophotometry using NanoDrop Lite (Thermo Scientific). The RT-PCR assay was performed on the StepOnePlus (Applied Biosystems) equipment. To analyze the gene expression of TYRP-1, a commercially available assay system (gene expression of TaqMan® assays; TYRP-1: Hs00167051_m1, Applied Biosystems) was used.

The test conditions were 48° C. for 30 minutes for reverse transcription, 95° C. for 10 minutes for activation of Ampli-Taq Gold® polymerase DNA, followed by 55 cycles of 94° C. for 15 seconds and 60° C. for 1 minute for denaturation and reheating, respectively. The relative amount of mRNA was calculated as described by Pfaffl (2001) and Livak & Schmittgen (2001).

Example 2.4: Statistical Analysis

For statistical analysis, variance analysis (ANOVA) was used. Dunnett's test was used when variance analysis detected significant differences between groups. In all the groups studied, those whose P values were less than 0.05 were considered statistically significant.

Example 2.5: Results

Figure 3:
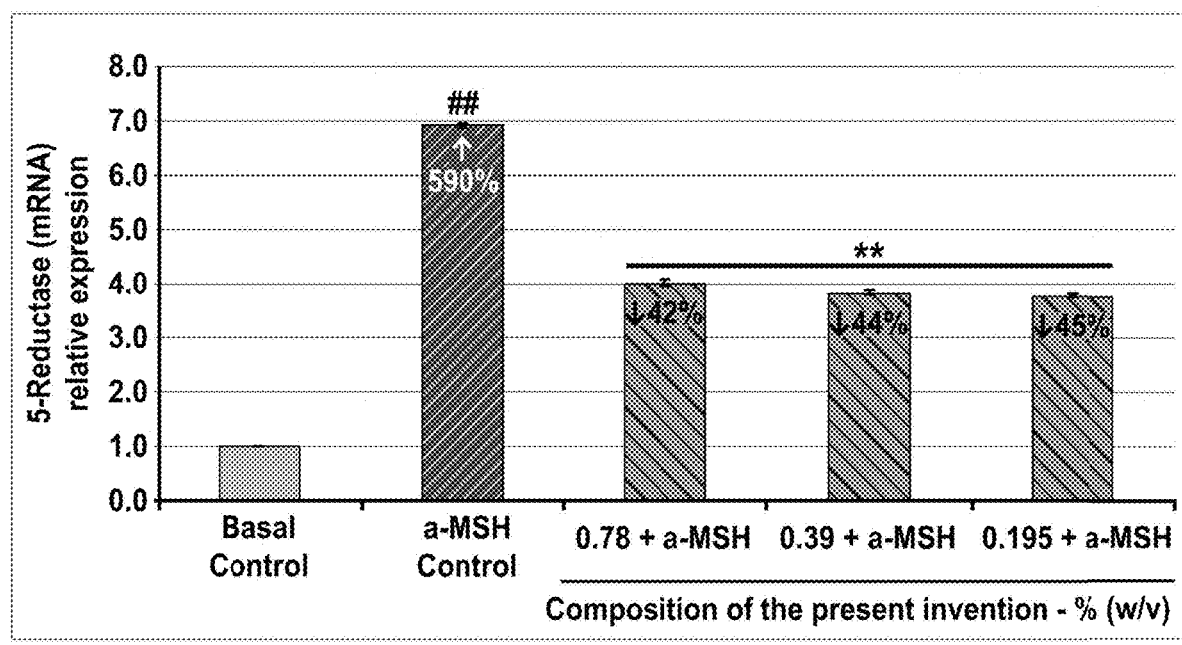
FIG. 3 shows a graph with the results of the effects of the composition of the present invention on the gene expression of TYRP-1 in human melanocytes culture after 24 hours of incubation.
Figure 4:
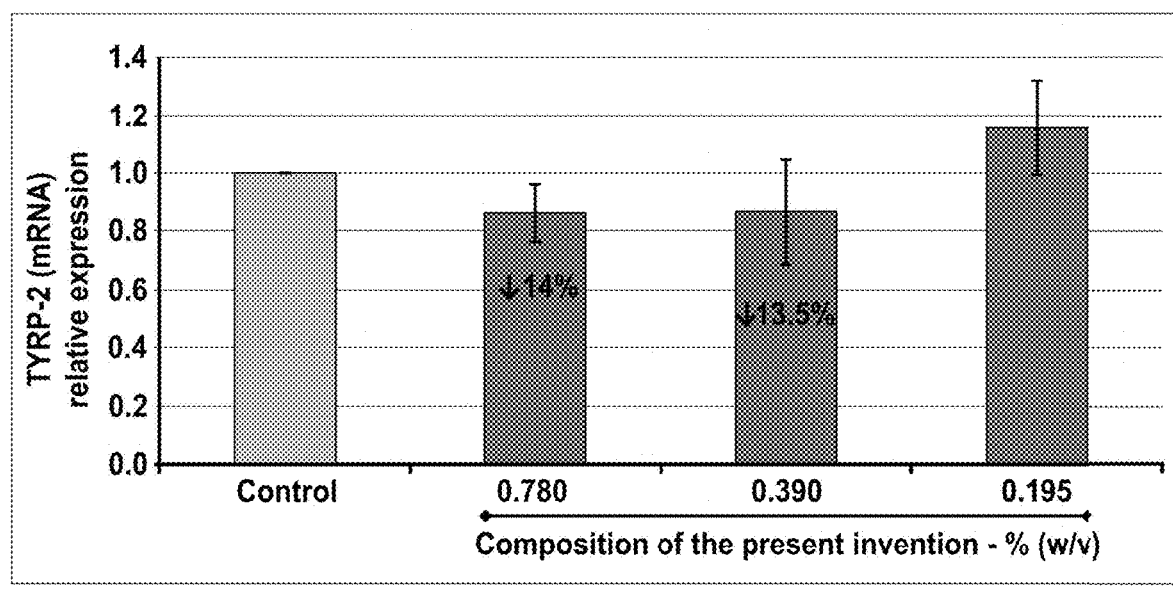
FIG. 4 shows a graph with the results of the effects of the composition of the present invention on the gene expression of TYRP-2 in "dark pigmented" human melanocytes culture after 24 hours of incubation.

The results obtained, shown in Table 2 below, and FIG. 3, expose the relative gene expression (mRNA) of TYRP-1. It is possible to observe that the cosmetic composition of the invention in the concentrations evaluated of 0.78 and 0.39% (w/v), was able to reduce the relative expression of TYRP-1 by 42, 44 and 45%, respectively, in relation to the Alpha-MSG Control group under the same conditions.

TABLE 2

| Concentration (% (w/v)) | V1 | V2 | V3 | V4 | Average | DP |
|---|---|---|---|---|---|---|
| Basal Control | 1.000 | 1.000 | 1.000 | 1.000 | 1.000 | 0.000 |
| Alpha-MSH Control | 6.928 | 6.854 | 6.940 | 6.897 | 6.905 | 0.038 |
| 0.78 + Alpha-MSH | 4.058 | 3.958 | 3.981 | 4.118 | 4.029 | 0.073 |
| 0.39 + Alpha-MSH | 3.858 | 3.806 | 3.870 | 3.796 | 3.832 | 0.037 |
| 0.195 + Alpha-MSH | 3.772 | 3.718 | 3.786 | 3.813 | 3.772 | 0.040 |

Example 3: Effects on the Gene Expression of TYRP-2 on "Dark Pigmented" Human Melanocytes Culture Example 3.1: Melanocytes Culture "Dark pigmented" human melanocytes (HEM-DP) were sown in 75 cm² bottles, cultivated and expanded in humid greenhouse at 37° C. in the presence of 5% $CO_2$, using specific culture medium. Upon reaching confluence, the cells were sown in plates of 06 wells for further incubation with the composition and evaluation of the proposed parameter.

Example 3.2: Incubation with the Cosmetic Composition of the Invention

Cell cultures were incubated with 3 non-cytotoxic concentrations of the cosmetic composition of the invention (0.78; 0.39; 0.195% (w/v)), previously determined through the MTT technique. The cells were kept in contact with the composition for 24 hours for subsequent cell lysate collection, extraction and relative quantification of mRNA. The control group was evaluated in parallel.

Example 3.3: Gene Expression of TYRP-2 by Real-Time PCR

After 24 hours of incubation with predetermined concentrations of the cosmetic composition of the invention, the total RNA was extracted using the PureLink™ RNA Mini Kit (Life Technologies) and quantified through spectrophotometry using NanoDrop Lite (Thermo Scientific). The RT-PCR assay was performed on the StepOnePlus (Applied Biosystems) equipment. To analyze the gene expression of TYRP-2, a commercially available assay system (gene expression of TaqMan® assays; TYRP-2 (Dopacromo-tautomerase): HS01098278_m1, Applied Biosystems) was used, primer and probe with proper base. The test was performed using the 1-Step TaqMan® RNA-to-CT™ (Applied Biosystems) kit.

The test conditions were 48° C. for 30 minutes for reverse transcription, 95° C. for 10 minutes for activation of AmpliTaq Gold® polymerase DNA, followed by 55 cycles of 94° C. for 15 seconds and 60° C. for 1 minute for denaturation and reheating, respectively. The relative amount of mRNA was calculated as described by Pfaffl (2001) and Livak & Schmittgen (2001).

Example 3.4: Statistical Analysis

For statistical analysis, variance analysis (ANOVA) was used. Dunnett's test was used when variance analysis detected significant differences between groups. In all the groups studied, those whose P values were less than 0.05 were considered statistically significant.

Example 3.5: Results

The results obtained, shown in Table 3 below, and FIG. 3, expose the relative gene expression (mRNA) of TYRP-2. It is possible to observe that the cosmetic composition of the invention evaluated in the concentrations of 0.78 and 0.39% (w/v), was able to reduce the relative expression of TYRP-2 by 14 and 13.5%, respectively, in relation to the Control group.

TABLE 3

| Concentration (% (w/v)) | V1 | V2 | V3 | V4 | Average | DP |
|---|---|---|---|---|---|---|
| Control | 1.000 | 1.000 | 1.000 | 1.000 | 1.000 | 0.000 |
| 0.78 | 0.804 | 0.763 | 0.983 | 0.895 | 0.861 | 0.098 |
| 0.39 | 1.005 | 0.623 | 0.836 | 0.994 | 0.864 | 0.179 |
| 0.195 | 1.011 | 1.303 | 1.017 | 1.283 | 1.154 | 0.161 |

Example 4: Example of Cosmetic Composition

The compounds used in the dermocosmetic formulation of the present invention cosmetic composition, the ranges of their respective weight/weight percentages and their respective functions are shown in Table 4.

TABLE 4

| Raw material | % | Function |
|---|---|---|
| Water | 59.22-95.00 | Vehicle |
| PEG-40 hydrogenated castor oil | 2.25-9.0 | Surfactant |
| Capric/Caprylic Triglyceride | 1.5-6.0 | Conditioning Agent |
| Glycerin | 1.5-6.0 | Humectant |
| ALPHA-ARBUTIN | 1.0-5.0 | Whitening Agent |
| Glucosyl Hesperidin | 0.25-2.0 | Conditioning Agent |
| Sodium hydroxide | 0.25-2.0 | pH adjuster |
| Phenoxyethanol | 0.25-2.0 | Preservative |
| Styrene/acrylates copolymer | 0.2-2.0 | Opacifier |
| Sodium PCA | 0.075-5.0 | Conditioning Agent |
| *Hypoxis Rooperi* Rhizome Extract | 0.02-10.0 | Conditioning Agent |
| Sodium Lactate | 0.02-0.3 | Humectant |
| Disodium EDTA | 0.05-0.3 | Chelation Agent |
| Benzotriazolyl Dodecyl p-Cresol | 0.05-0.3 | Photo-protector |
| Citric acid | 0.05-0.3 | pH adjuster |
| Arginine | 0.04-5.0 | Conditioning Agent |
| *Caesalpinia Spinosa* Gum | 0.03-5.0 | Film-forming Agent |
| Propylene glycol | 0.02-0.5 | Humectant |
| Aspartic acid | 0.02-5.0 | Conditioning Agent |
| Diglucosyl Gallic Acid | 0.02-5.0 | Conditioning Agent |
| PCA | 0.02-10.0 | Moisturizer |
| Biosaccharide Gum-2 | 0.01-10.0 | Conditioning Agent |
| Glycine | 0.01-5.0 | Conditioning Agent |
| Alanine | 0.01-5.0 | Conditioning Agent |
| Biosaccharide Gum-1 | 0.01-5.0 | Conditioning Agent |

TABLE 4-continued

| Raw material | % | Function |
|---|---|---|
| Potassium Sorbate | 0.01-5.0 | Preservative |
| Sodium Benzoate | 0.01-0.5 | Preservative |
| Methylisothiazolinone | 0.0083-0.5 | Preservative |
| Serine | 0.0080-5.0 | Conditioning Agent |
| Valine | 0.003-5.0 | Conditioning Agent |
| Glycine Soybean Oil | 0.003-5.0 | Emollient |
| Sodium Oleate | 0.0003-5.0 | Surfactant |
| *Humulus Lupulus* Strobile | 0.003-5.0 | Emollient |
| Isoleucine | 0.003-5.0 | Antistatic |
| Proline | 0.002-5.0 | Conditioning Agent |
| Threonine | 0.002-5.0 | Conditioning Agent |
| Hydrogenated Lecithin | 0.001-5.0 | Conditioning Agent |
| Histidine | 0.001-5.0 | Conditioning Agent |
| Phenylalanine | 0.001-5.0 | Conditioning Agent |
| Decapeptide-4 | 0.0001-5.0 | Conditioning Agent |

In a preferential embodiment, the compounds used in the formulation of the cosmetic composition of the present invention, their respective weight/weight percentages and their respective functions are shown in Table 5.

TABLE 5

| INCI | % | FUNCTION |
|---|---|---|
| Water | 75.7000 | Vehicle |
| Disodium EDTA | 0.1000 | Chelation Agent |
| Benzotriazole Dodecyl p-Cresol | 0.1000 | Photo-protector |
| PEG-40 hydrogenated castor oil | 4.5000 | Surfactant |
| ALPHA-ARBUTIN | 2.0000 | Whitening Agent |
| Glucosyl Hesperidin | 0.5000 | Conditioning Agent |
| Water | 2.9181 | Vehicle |
| Glycerin | 0.0300 | Humectant |
| Phenoxyethanol | 0.0300 | Preservative |
| Disodium EDTA | 0.0060 | Chelation Agent |
| Glycine Soybean Oil | 0.0060 | Emollient |
| Sodium Oleate | 0.0060 | Surfactant |
| Hydrogenated Lecithin | 0.0030 | Conditioning Agent |
| Decapeptide-4 | 0.0009 | Conditioning Agent |
| Glycerin | 1.2060 | Humectant |
| Water | 0.7500 | Vehicle |
| Diglucosyl Gallic Acid | 0.0440 | Conditioning Agent |
| Water | 2.2000 | Vehicle |
| Glycerin | 1.5000 | Humectant |
| *Hypoxis Rooperi* Rhizome Extract | 0.1200 | Conditioning Agent |
| *Caesaipinia Spinosa* Gum | 0.0600 | Film-forming Agent |
| Sodium Benzoate | 0.0100 | Preservative |
| Potassium sorbate | 0.0100 | Preservative |
| Water | 0.9740 | Vehicle |
| Phenoxyethanol | 0.0150 | Preservative |
| Biosaccharide Gum-1 | 0.0110 | Conditioning Agent |
| Sodium PCA | 0.1500 | Conditioning Agent |
| Sodium Lactate | 0.1200 | Humectant |
| Arginine | 0.0800 | Conditioning Agent |
| Aspartic Acid | 0.0520 | Conditioning Agent |
| PCA | 0.0427 | Moisturizer |
| Glycine | 0.0128 | Conditioning Agent |
| Alanine | 0.0120 | Conditioning Agent |
| Serine | 0.0080 | Conditioning Agent |
| Valine | 0.0064 | Conditioning Agent |
| Proline | 0.0040 | Conditioning Agent |
| Threonine | 0.0040 | Conditioning Agent |
| Isoleucine | 0.0040 | Antistatic |
| Histidine | 0.0016 | Conditioning Agent |
| Phenylalanine | 0.0016 | Conditioning Agent |
| Water | 0.5009 | Vehicle |
| Water | 0.9600 | Vehicle |
| Biosaccharide Gum-2 | 0.0250 | Conditioning Agent |
| Phenoxyethanol | 0.0150 | Preservative |
| Capric/Caprylic Triglyceride | 2.9946 | Conditioning Agent |
| *Humulus Lupulus* Strobile | 0.0054 | Emollient |
| Styrene/acrylates copolymer | 0.4000 | Opacifier |
| Water | 0.6000 | Vehicle |
| Methylisothiazolinone | 0.0083 | Preservative |
| Phenoxyethanol | 0.4255 | Preservative |
| Propylene glycol | 0.0575 | Humectant |

TABLE 5-continued

| INCI | % | FUNCTION |
|---|---|---|
| Water | 0.0088 | Vehicle |
| Citric acid | 0.1000 | pH adjuster |
| Sodium hydroxide | 0.5000 | pH adjuster |
| TOTAL | 100.0000 | |

Example 5: Conclusions

Referring to Example 1, it can be concluded that the cosmetic composition of the present invention was able to reduce by up to 88% (P<0.01) Endothelin-1 (ET-1) gene expression when compared to the parallel evaluation of the Control group.

Referring to Example 2, it can be concluded that the cosmetic composition of the present invention in human melanocytes culture and under stimulation conditions by the alpha-MSH hormone was able to reduce by up to 45% (P<0.01) to TYRP-1 gene expression when compared to the Alpha-MSH parallel evaluation of the Control group.

Considering the results presented in Example 3, the cosmetic composition of the invention, in a "dark pigmented" human melanocyte culture, was able to reduce by up to 14% the gene expression of TYRP-2, when compared to the parallel evaluation of the Control group.

Although certain embodiments have been specifically described, they were presented only in an exemplifying way, and there is no intention of limiting the scope of the invention. The claims accompanying this specification and its equivalents are considered to be covering such embodiments.

Finally, modifications of the present invention, evident to a person skilled in the art, such as adding or removing non-fundamental elements to its realization, can be carried out without moving away from the scope and spirit of the invention.

REFERENCES

1. Kobayashi et al. Tyrosinase related protein 1 (TYRP1) functions as a DHICA oxidase in melanin biosynthesis. The EMBO Journal vol. 13 no. 24 pp. 5818-5825, 1994.
2. Tsukamoto et al. A second tyrosinase-related protein, TYRP-2, is a melanogenic enzyme termed DOPAchrome tautomerase. The EMBO Journal vol. 11 no. 2 pp. 519-526, 1992.

The invention claimed is:

1. A cosmetic composition comprising a combination of α-arbutin, glucosyl hesperidin, diglucosyl gallic acid, *Hypoxis rooperi* rhizome extract, *Caesalpinia spinosa* Extract Gum, *Humulus lupulus* (hops) Strobile and decapeptide-4.

2. The cosmetic composition according to claim 1, wherein said composition further comprises moisturizers, chelation agents and/or cosmetically acceptable excipients.

3. The cosmetic composition according to claim 2, wherein the cosmetically acceptable excipients are selected from the group consisting of: surfactants, preservatives, conditioning agents, humectants, emollients, film-forming agents, pH adjuster agents, vehicles, and combinations thereof.

4. The cosmetic composition according to claim 3, wherein the concentration of the pH adjuster agents range from 0.05 to 2.0% (w/w).

5. The cosmetic composition according to claim 3, wherein the concentration of the conditioning agents ranges from 0.0001 to 10.0% (w/w).

6. The cosmetic composition according to claim 3, wherein the concentration of the preservatives ranges from 0.0083 to 5.0% (w/w).

7. The cosmetic composition according to claim 3, wherein the concentration of the emollients ranges from 0.003 to 5.0% (w/w).

8. The cosmetic composition according to claim 2, wherein the concentration of the moisturizers ranges from 0.02 to 10.0% (w/w).

9. The cosmetic composition according to claim 3, wherein the concentration of the film-forming agents ranges from 0.03 to 5.0% (w/w).

10. The cosmetic composition according to claim 3, wherein the concentration of the humectants ranges from 0.02 to 6.0% (w/w).

11. The cosmetic composition according to claim 3, wherein the concentration of the surfactants ranges from 0.0003 to 9.0% (w/w).

12. The cosmetic composition according to claim 2, wherein the concentration of the chelation agents ranges from 0.05 to 0.3% (w/w).

13. The cosmetic composition according to claim 3, wherein the concentration of the vehicles ranges from 59.22 to 95% (w/w).

14. The cosmetic composition according to claim 3, wherein the pH adjuster agents include sodium hydroxide or citric acid.

15. The cosmetic composition according to claim 3, wherein the conditioning agents are selected from the group consisting of: hydrogenated lecithin, biosaccharide gum-1, sodium PCA, arginine, aspartic acid, glycine, alanine, valine, proline, threonine, histidine, phenylalanine, biosaccharide gum-2, and caprylic/capric triglyceride.

16. The cosmetic composition according to claim 3, wherein the preservatives are selected from the group consisting of: phenoxyethanol, potassium sorbate, methylisothiazolinone, sodium benzoate, and mixtures thereof.

17. The cosmetic composition according to claim 3, wherein the emollients include glycine and the moisturizers include PCA.

18. The cosmetic composition according to claim 3, wherein the humectants are selected from the group consisting of: glycerin, sodium lactate, and propylene glycol.

19. The cosmetic composition according to claim 3, wherein the surfactants are selected from the group consisting of: hydrogenated castor oil, and sodium oleate.

20. The cosmetic composition according to claim 2, wherein the chelation agents are selected from the group consisting of: EDTA, disodium EDTA, tetrasodium EDTA and mixtures thereof.

21. The cosmetic composition according to claim 3, wherein the vehicles are selected from the group consisting of: water, esters, mineral oil, vegetable oils, and mixtures thereof when in an emulsified system.

22. A dermocosmetic formulation comprising the composition according to claim 1 presented as a solution, a suspension, a cream, a gel, a lotion or a serum.

23. The cosmetic composition according to claim 1, wherein the cosmetic composition is used for action on melanin production mechanisms by the gene expression of tyrosinase-related proteins (TYRP-1 and TYRP-2) and Endothelin-1 (ET-1).

24. The cosmetic composition according to claim 23, wherein the cosmetic composition is used in combating skin blemishes.

25. The cosmetic composition according to claim 23, wherein the cosmetic composition is used in combating melasma.

* * * * *